United States Patent [19]

Murayama

[11] Patent Number: 5,401,495

[45] Date of Patent: *Mar. 28, 1995

[54] TEETH WHITENER

[75] Inventor: Ron Murayama, Laguna Niguel, Calif.

[73] Assignee: Natural White, Inc., Laguna Niguel, Calif.

[*] Notice: The portion of the term of this patent subsequent to Jun. 16, 2009 has been disclaimed.

[21] Appl. No.: 747,387

[22] Filed: Aug. 20, 1991

Related U.S. Application Data

[63] Continuation of Ser. No. 582,899, Oct. 10, 1990.

[51] Int. Cl.$^6$ .................................. A61K 7/16
[52] U.S. Cl. ........................................ 424/49; 424/53
[58] Field of Search ............... 424/49, 53; 252/186.3; 514/616

[56] References Cited

U.S. PATENT DOCUMENTS

| | | | |
|---|---|---|---|
| 2,798,053 | 7/1957 | Brown | 424/81 |
| 3,499,844 | 3/1970 | Kibbel | 252/186.3 |
| 3,956,480 | 5/1976 | Dichter | 424/54 |
| 4,017,411 | 4/1977 | Diehl et al. | 252/186.29 |
| 4,032,627 | 6/1977 | Suchan et al. | 106/35 |
| 4,122,162 | 10/1978 | Muehlemann | 424/52 |
| 4,130,501 | 12/1978 | Lutz et al. | 252/186.43 |
| 4,144,322 | 3/1979 | Cordon et al. | 424/49 |
| 4,152,420 | 5/1979 | Gaffar et al. | 424/56 |
| 4,187,287 | 2/1980 | Schreiber | 424/49 |
| 4,187,288 | 2/1980 | Cordon | 424/49 |
| 4,273,759 | 6/1981 | Gaffar et al. | 424/54 |
| 4,428,928 | 1/1984 | Muhler et al. | 424/49 |
| 4,482,535 | 4/1985 | Sugar et al. | 424/49 |
| 4,512,743 | 4/1985 | Santucci et al. | 106/35 |
| 4,643,678 | 2/1987 | Hansen | 106/35 |
| 4,647,451 | 3/1987 | Piechota | 425/52 |
| 4,661,070 | 4/1987 | Friedman | 433/203.1 |
| 4,788,052 | 11/1988 | Ng et al. | 424/53 |
| 4,839,157 | 6/1989 | Mei-King | 424/53 |
| 5,011,682 | 4/1991 | Elliott | 424/52 |
| 5,122,365 | 6/1992 | Murayama | 424/49 |

FOREIGN PATENT DOCUMENTS 0827331  2/1960  United Kingdom .

OTHER PUBLICATIONS

Cosmetics and Toiletries, vol. 91, Sep. 1987, "Stability of Hydrogen Peroxide in Certain Pharmaceutical Gels", (A. I El Assay, A Abd Elbary, and Y. H. Hamza), pp. 54–56.

Endodontics and Dental Traumatology, vol. 4, No. 1, 1988, "Incidence of External Root Resorption and Esthetic Results in 58 Bleached Pulpless Teeth" (S. Friedman, et al.), pp. 23–26.

Pediatric Dentristy, vol. 7, No. 3, 1985, "Color Change Following Vital Bleaching of Tetracycline—stained Teeth" (Carolyn Wilson, et al.), pp. 205–208.

J. Dental Research, vol. 60, No. 5, May 1981, "Pulpal Reaction to Bleaching of Teeth in Dogs" (Seale, et al.), pp. 948–953.

*Primary Examiner*—D. Gabrielle Philan
*Assistant Examiner*—William E. Benston
*Attorney, Agent, or Firm*—Kokjer, Kircher, Bowman & Johnson

[57] ABSTRACT

A three component system and method for whitening teeth comprising a pre-conditioning mouth rinse, a bleaching gel, and a polishing and pigmenting paste wherein each component is applied to the teeth independently and in sequential order.

18 Claims, No Drawings

TEETH WHITENER

This is a Continuation application of U.S. patent application Ser. No. 582,899, filed Oct. 10, 1990, which is incorporated herein by reference.

This invention relates in general to teeth whitening dentrifices and more particularly to a new system containing a plurality of substances used in combination that is useful for whitening and polishing human teeth.

For a variety of reasons it has become desirable for a person's teeth to appear bright or "white." Society places a high value on the "whiteness" of one's teeth. One whose teeth are white may enjoy more personal confidence and satisfaction and may even enjoy greater social acceptance. In many business situations, such as acting and television newsreporting, a person's appearance is of the utmost importance in securing employment and having "white" teeth is know to be an asset.

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. These hydroxyapatite crystals form microscopic hexagonal rods or prisms that make up the enamel surface. As a result, the surface of the enamel layer presents microscopic spaces or pores between the prisms. It is believed that this porous nature of the enamel layer is what allows staining agents and discoloring substances to permeate the enamel and discolor the tooth. These remaining substances can occupy the microscopic spaces and eventually alter the color of the tooth.

Many substances that a person confronts or comes in contact with on a daily basis can "stain" or reduce the "whiteness" of one's teeth. In particular, the foods, tobacco products and fluids that one consumes tend to stain one's teeth. These products or substances tend to accumulate on the enamel layer of the tooth and for a pellicle film over the teeth. These staining and discoloring substances can then permeate the enamel layer. This problem occurs gradually over many years, but imparts a noticeable discoloration of the enamel of one's teeth. So long as the discolored teeth are still healthy and do not pose any health risk or problem, a product or substance that would whiten the discolored teeth would be advantageous.

It is also essential that a teeth whitening product that is to be used at home or in private by the consumer be safe and easy to use. A product for home use cannot utilize some of the compositions or products for whitening teeth that are available for use by a trained dental professional. For example, a 35% hydrogen peroxide bleaching agent is utilized by many dental practitioners to bleach severely discolored teeth. Such a concentrated solution of hydrogen peroxide would be irritating and potentially dangerous for home use by the consumer. Products and substances that are presently available to whiten teeth include a variety of different ingredients, but the primary active ingredient is an abrasive agent formulated into a gel or paste. These abrasive gel type products "polish" the enamel layer of the teeth to which it is applied and give it a more lustrous sheen and partially scrub away materials that stain the tooth enamel. These abrasive products are not able to perform all of the desired functions in a fully satisfactory manner.

It is therefore a primary object of the present invention to provide a system for whitening teeth that is more effective in whitening teeth and safer to use than existing products available to the consumer.

It is another object of the present invention to provide a system for whitening teeth that includes a cleansing mouth rinse, a bleaching substance and a pigmenting agent as well as an abrading and polishing agent to more completely and more efficiently whiten teeth than known products.

It is still another object of the present invention to provide a complete system for whitening the enamel of human teeth that is safe for home use and a method of use that can easily be performed by the consumer without the assistance of a trained dental professional.

It is a further object of the present invention to provide a system and method for whitening human teeth where the component parts of the system are to be used in a sequential manner to cosmetically whiten a person's teeth.

It is still a further object of the present invention to provide a teeth whitening product that includes an effective quantity of a bleaching agent such as hydrogen peroxide in a concentration that can be safely and comfortably used at home by the consumer.

It is yet a further object of the present invention to provide a product for whitening teeth that includes an effective quantity of hydrogen peroxide to bleach teeth in a manageable and convenient gel medium that can be applied with the use of an appropriate applicator.

It is an aim of the present invention to provide a product for whitening teeth that includes a pigmenting substance that is of a small enough particle size to fit into the pores or spaces between the hydryxyapatte crystals or enamel prisms that make up the enamel layer.

It is another aim of the present invention to provide a teeth whitening product that utilizes a pigmenting substance that imparts a white pigment to the enamel layer of the tooth and that also functions as an abrasive substance to polish the teeth.

It is a further aim of the present invention to provide a system for whitening teeth that can be safely and effectively be used on a daily basis to prevent further discoloration of the user's teeth.

Other and further objects of the invention, together with the features of novelty appurtenant thereto, will appear in the course of the following description of the invention.

The present invention is directed to an improved system and method for whitening teeth that has three separately formulated components having four primary active ingredients to serve as a complete and effective teeth whitener. The system includes a conditioning mouth rinse, a bleaching gel, and a polishing and pigmenting composition, wherein each component is applied independently and sequentially. In accordance with the invention, the first component is a teeth cleansing mouth rinse formulated by preparing a dilute, aqueous solution of acetic acid in combination with flavor enhancers, a preservative, a surfactant and mixtures thereof. The second component of the system is a gel capable of bleaching teeth enamel and is formulated as a combination of hydrogen peroxide, a gelling agent capable of maintaining the stability of the hydrogen peroxide over a period of time, a neutralizing agent, a thickening agent and mixtures thereof. The third component of the teeth whitening system and method is a polishing cream or paste that includes a pigmenting agent. The polishing cream is formulated by combining deionized water, a carrier, an abrasive polishing agent, flavor enhancers, thickening agents, surfactants, a pigmenting agent and mixtures thereof. Alumina silicates are most useful as the abrasive and polishing agent and most preferred are synthetic precipitated amorphous alumina silicates sold under the trademarks ZEO-49 or ZEODENT 113 by the J. M. Huber Corp. of Harve de Grace, Md. The preferred carrier is glycerin and the most preferred pigmenting agent is titanium dioxide.

The flavor enhancers used can be any substance that imparts a flavor of sweetness to the product by addition of a relatively small amount of the substance. Examples include saccharin, sodium saccharin, methyl salicylate, menthol crystals, mint flavoring agents, cinnamon flavoring agents and the like. The chemicals that impart such flavors are well known to those skilled in the art and are readily available. Any suitable preservative can be utilized such as sodium benzoate or other preservatives known to one skilled in the art. Suitable surfactants are Tween-20, which is a well known and recognized tradename for polyoxyethylene (20) sorbitan Monolaurate, sodium dodecyl sulfate or sodium lauryl sulfate in amounts capable of improving the solubility and dispersal of the products added to the components.

The components of the present teeth whitening system are to be used in a sequential fashion. The user first rinses his mouth and concomitantly his teeth with the conditioning mouth rinse of the invention. This is followed by applying the bleaching gel onto the teeth. This second component is applied onto the teeth for approximately 1-4 minutes and then the teeth are rinsed with water. Finally, the polishing and pigmented cream is brushed onto the teeth. This component of the system is brushed onto the teeth for about 1-3 minutes and left on the teeth as long as possible, preferably overnight.

The bleaching gel and the polishing and pigmented cream may alternatively be used alone or in combination with each other, as well as in the overall whitening system.

In accordance with the invention, a three component teeth whitening system is provided. Each component is formulated and packaged separately. In formulating the components, pharmaceutical grade reagents, if available, should be used throughout and all necessary safety and sterility procedures should be employed for a product that will be used in contact with human teeth and oral tissues.

The first component of the teeth whitening system is a conditioning mouth rinse. This mouth rinse is comprised generally of an aqueous dilution of acetic acid. The preferred concentration range of the acetic acid in the solution is between 1%-3% and is most preferably between 0.5%-1.5% acetic acid. Normal white distilled or household vinegar can be used to prepare the mouth rinse.

The mouth rinse may include a flavor enhancer such as sodium saccharine or any other sweetener such as aspartame, methyl salicylate or the like. Sodium saccharine can be added in a concentration range of between 0.05%-0.5% to impart a sweet taste to the mouth rinse. The preferred amount of sodium saccharine has a 0.2% final concentration in the mouth rinse. Additional flavor enhancers so as to impart a particular flavor and/or aroma to the rinse can also be added. Particularly useful flavorings are menthol, wintergreen, spearmint, cinnamon or other appropriate and acceptable flavors. The chemical entities that create these flavor substances should be added in an amount sufficient to impart a flavor to the product. The most useful range of concentration for flavorings is between 0.02%-1% final concentration in the rinse. Different flavors may require different amounts to be added to create a noticeable flavor. In any event, a flavor enhancer should be a relatively small portion of the overall rinse.

It may also be necessary to include a preservative in the mouth rinse formulation to retard any bacterial growth or other potential disease causing agent to grow in the rinse. Any suitable preservative useful in the food industry can be utilized. Especially useful is sodium benzoate in a concentration of between 0.2%-2% in the conditioning rinse. The most preferred concentration of sodium benzoate in the oral conditioning rinse is 0.3%.

Another useful additive that may be added to the conditioning mouth rinse is a surfactant or other surface-active agent in a relatively small quantity to assist in the solubility and dispersal of the added substances to the basic rinse. Particularly useful are Tween-20, which is a well known and recognized tradename for polyoxyethylene (20) sorbitan monolaurate, sodium dodecyl sulfate, sodium lauryl sulfate and like compositions.

In preparing the conditioning mouth rinse, deionized water is first heated to about 80° C. and any preservative or sweetener is dissolved therein. The solution is then allowed to cool and an appropriate amount of 5% acetic acid is added to obtain the desired final concentration. At this point, a surfactant is added and any flavoring chemical or composition is likewise added. The resulting solution is stirred until all of the substances are fully dissolved. The rinse is now ready for its use in cleansing and debriding the pellicle film that accumulates on the enamel of teeth. The application of this rinse to a person's teeth pre-conditions the enamel layer of the teeth to be more accessible to the actions of the subsequent components of the whitening system.

The second component of the teeth whitening system of the present invention is a bleaching gel. The active ingredient in this bleaching component is hydrogen peroxide. This component of the whitening system uses a relatively low concentration of hydrogen peroxide in a gel form. A high concentration of hydrogen peroxide could not be used safely by the typical consumer and therefor the useful range of hydrogen peroxide in the gel is between 1%-10% hydrogen (by weight). The most preferred range is between 3%-6.5% and the most preferred concentration is 6% in the gel. Hydrogen peroxide generally has a pH of between 3-6 and is preferably maintained around 6. The hydrogen peroxide is prepared as a gel to provide a safe and easy form in which it may be applied onto the user's teeth. A liquid hydrogen peroxide formulation would be irritating to the gums and gigival tissues and would therefore not be as useful as the preferred easy to use gel form in accordance with the instant invention.

A suitable gelling agent to form the bleaching gel of the whitening system must be one that can maintain the stability of the hydrogen peroxide over a period of time. Hydrogen peroxide is known to be unstable in any form other than its aqueous form. The gelling agent has a pH adjustability between 2 and 7 to ensure the stability of the hydrogen peroxide. Any gelling agent that has these properties and that can produce a viscous gel with water would be suitable for this formulation.

A particularly useful gelling agent is a copolymer of acrylic acid cross-linked with polyallyl sucrose, as described in U.S. Pat. No. 2,798,053, issued on Jul. 2, 1957 and assigned to B. F. Goodrich, Inc. Other suitable gelling agents are described in U.S. Pat. No. 3,639,574 issued on Feb. 1, 1972 to Schmolka, British Patent No. 827,331 and U.S. Pat. No. 3,499,844 issued on Mar. 10, 1970 to Kibble, et al. These references generally describe gelling agents that produce stable gels with hydrogen peroxide. These gels generally comprise polyoxyethylene polypropylene block copolymers, organic polymer acids colloids including polyuronic acids, carboxypolymethylene compounds and polyester resins containing three carboxyl groups, such as partially hydrolyzed polyacrylates or polymethacrylates and copolymers thereof.

The most preferred gelling agent is a water dispersible copolymer of acrylic acid cross-linked with approximately 0.75% to approximately 1.5% polyallyl sucrose that is sold under the trademark CARBOPOL 934 by B. F. Goodrich. This gelling agent is neutralized with triethanolamine or another suitable alkalizing agent as discussed in U.S. Pat. No. 3,499,844 to achieve a pH of the final product around 3.5. In order to obtain the most useful gel for use in the present invention a sufficient amount of non-ionic cellulose or gum is added to the gel to improve the physical stability of the gel. This is basically a thickening agent and hydroxyethylcellulose gum, hydroxypropylcellulose gum or carboxymethyl cellulose work effectively and are preferred, although other like products would have utility.

In preparation, the bleaching gel that is the second component of the teeth whitening system preferably comprises 6% by weight of hydrogen peroxide, 2% of CARBOPOL 934 (an acrylic acid copolymer cross-linked with polyallyl sucrose), 1% of triethanolamine, 1% by weight of hydroxyethylcellulose, and the remainder is deionized water. This formulation is prepared by first combining an appropriate amount of a 35% aqueous solution of hydrogen peroxide with deionized water. This mixture is slowly stirred and CARBOPOL 934 is gradually added. After the gelling agent has become thoroughly dispersed in the hydrogen peroxide solution, the hydroxyethylcellulose is slowly added until it dissolves. Finally, 99% triethanolamine is diluted in a 1:1 ratio with deionized water and slowly added to the gelled solution to achieve a final pH of approximately 3.5. The resulting compound is clear, homogeneous, stable and viscous gel.

The bleaching gel can then be placed on an applicator such as a cotton swab and applied onto the teeth for 1-4 minutes. Alternatively, the bleaching gel may be applied directly to the teeth and allowed to remain in contact therewith for a like amount of time. The gel is then removed by rinsing with water.

The third component of the teeth whitening system is a polishing paste that includes a white pigmenting agent. This compound is formulated into a paste or cream that can be placed on a toothbrush and brushed onto the teeth. The polishing agent utilized in this compound is a dental abrasive that can debride and physically scrub the external surface of teeth. This scrubbing action removes filmy bacterial and plaque layers as well as some of the stains and discoloring pigments that are found on teeth that cause the undesired discoloration. These polishing agents also microabrade the tooth so as to polish the teeth to give the enamel a more lustrous appearance and a higher optical sheen. This microabrasion action enhances the scrubbed teeth's ability to reflect white light and thereby appear brighter.

The most useful type of debriding and polishing agent for use in this compound are alumina silicate particles. The preferred alumina silicates are those synthetic precipitated alumina silicates that have an average particle size of between 1-100 microns, an oil absorption of approximately 25 cc-75 cc/100 g as determined by the Linseed Oil Rub-Out Method, a surface area of between 100-300 square meters per gram of material as determined by the BET Method, and a sodium sulfate concentration of less than 5%. The most preferred alumina silicate particles for use in this invention are synthetic precipitated amorphous alumina silicas having an average particle size of approximately 9 microns, an oil absorption of 90 cc/100 g, a surface area of approximately 250 square meters/g and a sodium sulfate concentration of approximately 1% by weight. More particularly, the synthetic alumina silicas provided by the J. M. Huber Corp. of Harve de Grace, Md. under the trademarks ZEO-49 or ZEODENT-113 have been employed with good results.

The pigmenting agent that is included in the formulation of the polishing and pigmented cream or paste is titanium dioxide. This pigmenting agent is particularly useful because of its brilliant opaque white color and its extremely small particle size. Other pigmenting agents with these qualities would be equally applicable and useful to this invention. A further benefit of titanium dioxide as the pigmenting agent is its ability to also function as a polishing or abrading agent when it is being applied. This further enhances the polishing features of the complete compound. Titanium dioxide particles that are useful in the present formulation have an approximate size of between 0.1-1.5 microns and most preferably have a particle size between 0.1-0.2 microns. A pigmenting agent having this approximate size allows the pigmenting agent to be absorbed by the enamel of the teeth and occupy the space between the hydroxyapatite crystals or prisms that make up the enamel layer of the teeth. Thus, this pigment competes with the substances that tend to stain or discolor teeth by filling the space between the prisms with a white pigment instead of an undesired color pigment. This has the ultimate effect of "staining" the teeth white by absorption or masking of other discolorations.

The polishing and pigmented compound is prepared as a cream or paste, but could be prepared in gel form. The primary polishing agents, ZEO-49 or ZEODENT-113, are most useful if they comprise between 1%-35% of the compound and have a preferred concentration range of between 10%-30% and a most preferred range of between 15%-27%. A useful concentration range for the titanium dioxide is between 15%-25% with the preferred range being between 20%-25% and the most preferred concentration being approximately 23%.

The remaining components that form this compound are a carrier, deionized water, a thickening agent, a surfactant, a preservative and flavor enhancers. A wetting agent such as TEXAPON VHC needles can also be included to assist in the dispersal and solubility of the titanium dioxide and other inorganic compounds.

The carrier is preferably glycerin and deionized water, but other suitable carriers can be utilized. When glycerin is used, a useful concentration range is between 20%-80% and preferably between 25%-50%. Deionized water typically makes up approximately 5%-40% of the compound and most preferably approximately 15% of the compound.

The preferred thickening agent is a cellulose gum as previously described and is present in a concentration range of between approximately 0.1%–2% final concentration in the compound. A most useful thickener for use in this polishing and pigmenting cream is ZEOTHIX powder from the J. M. Huber Co. Any surfactant may be utilized that is safe for contacting with human oral cavities and that assists in the dispersal and dissolution of the added compounds. Most useful are sodium dodecyl sulfate, sodium lauryl sulfate, TWEEN-20 and TEXAPON VHC. The most useful in formulating the polishing and pigmented cream is TEXAPON VHC. The surfactant is added to the formulation is a concentration range of between 0.001%–0.1%.

Flavor enhancers may also be added to the polishing and pigmented cream and are preferably added in a total concentration range of between 0.1%–10%. Particularly useful flavor enhancers are sweeteners such as saccharin, sodium saccharin, sorbitol, methyl salicylate, aspartame and like substances. Other substances that impart a particular flavor to the cream may also be employed such as menthol crystals, wintergreen, spearmint, mint, or cinnamon flavors, among others.

The polishing and pigmented cream is prepared by combining the desired amount of deionized water, glycerin and a flavor enhancer, such as Sorbitol in a 70% stock solution, in a clean container and allowed to stir for approximately 1 hour. The desired amounts of a surfactant such as SDS, and other flavor enhancers such as methyl salicylate and menthol crystals are then added and the resulting solution is further stirred for 30 minutes. This solution is then stored and referred to as Stock Solution A.

Stock Solution A is then slowly stirred and the desired amount of titanium dioxide is added gradually thereto over the course of approximately 1 hour. The resulting suspension is stirred for an additional 30 minutes and the polishing agent is then added gradually, but with vigorous mixing, to the solution over a period of approximately 1 hour. This results in a slightly viscous solution and the thickening agent is added and any additional polishing agents are added gradually to the solution to obtain the desired viscosity.

In use, approximately 1–5 g of the polishing and pigmented cream is applied to a toothbrush and brushed vigorously onto the teeth. Brushing is continued for 1–3 minutes and is occasioned by a brilliant white lather that is generated by proper brushing and that should be maintained for the entire brushing sequence. The cream should be allowed to remain on the teeth for as long as possible, preferably overnight. This cream further abrades the pellicle film on the enamel while also polishing the enamel to create a lustrous sheen on the teeth. The pigment is absorbed into the enamel prisms and "stains" the enamel a more brilliant white and masks already present discolorations in and on the enamel layer of the teeth. This part of the teeth whitening system follows the application of the two previous substances, but could also be used alone.

In accordance with the present invention, the complete teeth whitening system, including the mouth rinse, bleaching gel and polishing and pigmented cream, are to be used on a daily basis with a noticeable whitening of the user's teeth within a short period of time following regular use. It is also envisioned that the bleaching gel and the polishing and pigmented cream be used individually or in combination with each other, apart from their use in the complete teeth whitening system.

The present invention is further illustrated by the following examples:

EXAMPLE 1

One formulation of the conditioning mouth rinse is prepared as follows:

To 63 parts deionized water, 30 parts of a 5% acetic acid solution is added to obtain a final acetic acid concentration of 1.5%. This solution is slowly mixed and a quantity sufficient to obtain 5 parts of aspartame in the solution is added. Menthol crystals are added in a quantity sufficient to obtain 0.5 parts menthol in the final solution and 0.3 parts of sodium benzoate is also added to the solution. TWEEN-20 is added to obtain 0.2 parts surfactant in the final solution and 1 part sodium benzoate is added to the final solution as a preservative. This solution is stirred until all additives are completely dissolved and a clear liquid results. This mouth rinse is packaged in an appropriate, clean container and is ready for use.

A sufficient quantity of the mouth rinse is placed in the user's mouth and is caused to come in contact with the user's teeth by normal methods employed in mouth rinses.

Use of this mouth rinse cleanses the teeth of some of the accumulated pellicle film that builds up on human teeth and that commonly contains discoloring or stain causing substances.

EXAMPLE 2

One formulation of the bleaching gel of the present invention is prepared as follows:

In the final gel containing 100 parts of materials, 14.4 parts of a 35 aqueous solution of hydrogen peroxide is added to 83.025 parts of deionized water. This solution is slowly stirred and 1.75 parts of CARBOPOL 934, a copolymer of acrylic acid cross-linked with 1% by weight of polyallyl sucrose having 5.8 allyl groups per molecule, is added. After the CARBOPOL 934 has dissolved in the solution, about 0.2 parts of hydroxyethylcellulose is slowly added and dissolved. Triethanolamine is then added to obtain a viscous gel that has a pH of around 3.5.

This bleaching compound is a viscous gel and is to be placed on an applicator or cotton swab for applying the gel onto the teeth. Approximately 1–5 grams of the gel is to be applied to the applicator and allowed to remain on the teeth for 3 minutes. This compound gently bleaches the teeth enamel and removes some of the discoloring stains and pigments.

EXAMPLE 3

One formulation of the polishing and pigmented cream of the present invention is prepared as follows:

A sufficient quantity of a reagent referred to as stock solution A is first prepared. On a weight/volume basis, 300 grams of deionized water is combined with 135 grams of a 70% aqueous solution of Sorbitol and 900 grams of glycerin. This solution is mixed and stirred for 1 hour and then 1.5 grams of sodium lauryl sulfate, 3.0 grams of sodium saccharine, 7.0 grams of methyl salicylate and 2.8 grams of menthol flavor crystals are added and stirred for an additional 30 minutes. The resulting clear liquid is stock solution A.

To a clean container, 208 grams of stock solution A is mixed with 100 grams of titanium dioxide particles. This solution is stirred for 30 minutes and 92 grams of ZEO-49 is added with vigorous mixing over 1 hour. The resulting solution is slightly viscous and approximately 1.5 grams of hydroxyethylcellulose and 1.5 grams of ZEOTHIX is also added to obtain the desired viscosity. The cream is then packaged in a appropriate container for use on a daily basis.

This cream is then placed on a toothbrush and is brushed and burnished onto the user's teeth. Approximately 1-5 grams of the cream is placed on the brush and is brushed on the teeth for 3 minutes. The brushing is occasioned by a brilliant white lather that is maintained throughout the brushing period. The cream is then rinsed away with water leaving the teeth with a bright, white appearance and a lustrous sheen after regular use.

EXAMPLE 4

The preferred formulation of the three components is as follows:

|  | Quantity (%) (By Weight) |
|---|---|
| Conditioning Mouth Rinse | |
| Deionized Water | 97.87 |
| Sodium Saccharin | 0.05 |
| Sodium Benzoate | 0.30 |
| 5% White Distilled Vinegar | 1.50 |
| Tween 20 | 0.250 |
| Menthol Crystals | 0.030 |
| Bleaching Gel | |
| Deionized water | 78.°6 |
| Carbopol 934 | 2.00 |
| 35% Hydrogen Peroxide | 17.14 |
| Deionized Water | 1.00 |
| Triethanolamine (99%) | 1.00 |
| Polishing and Pigmenting Cream | |
| Deionized Water | 14.67 |
| Sodium Saccharine | 0.10 |
| Sodium Benzoate | 0.50 |
| Glycerin | 29.00 |
| Caroxymethylcellulose-7MF | 0.50 |
| Sorbitol (70% aqueous) | 8.00 |
| Zeo-49 | 23.00 |
| Titanium Dioxide | 23.00 |
| Texapon VHC needles | 0.06 |
| Zeothix 265 | 0.80 |
| Methyl Salicylate | 0.26 |
| Menthol Crystals | 0.11 |

Each component is prepared and used as described in Example 1-3.

From the foregoing, it will be seen that this invention is one well adapted to attain all the ends and objects hereinabove set forth together with other advantages which are obvious and which are inherent to the invention.

It will be understood that certain features and subcombinations are of utility and may be employed without reference to other features and subcombinations. This is contemplated and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A three component system for whitening human teeth wherein each component is applied to the teeth in a sequential manner, said three component system comprising:

a first component comprising a conditioning mouth rinse capable of cleansing the surface of said teeth;

a second component comprising a viscous bleaching gel including an effective concentration of hydrogen peroxide for bleaching said teeth, said hydrogen peroxide present in an amount ranging from 1 to 10% by weight of the total gel; and a third component comprising a viscous polishing composition including an abrasive substance for polishing said teeth and a pigmenting agent capable of imparting a white color to said teeth, whereby said conditioning rinse, said bleaching gel and said polishing composition are applied individually and seriatim to said teeth.

2. The system as set forth in claim 1 wherein said conditioning rinse comprises a dilute aqueous solution of acetic acid.

3. The system as set forth in claim 2 wherein said acetic acid is present in said rinse at a concentration of approximately 1.5 percent.

4. The system as set forth in claim 1 wherein said conditioning rinse further includes substances selected from the following: flavor enhancers, preservatives, surfactants and mixtures thereof.

5. The system as set forth in claim 4 wherein said flavor enhancers are selected from the group consisting of sweeteners and flavoring chemicals, said sweeteners are selected from the group consisting of saccharin, sodium saccharin, methyl salicylate, sorbitol and aspartame, said flavoring chemicals are selected from the group consisting of chemicals imparting the flavor of menthol, spearmint, wintergreen and cinnamon, said preservatives selected from the group consisting of sodium benzoate, and said surfactants are selected from the group consisting of polyoxyethylene (20) sorbitan monolaurate, sodium dodecyl sulfate, sodium lauryl sulfate and mixtures thereof.

6. The system as set forth in claim 1 wherein said effective concentration of said hydrogen peroxide in said gel is between 3 percent and 8 percent.

7. The system as set forth in claim 6 wherein said concentration of said hydrogen peroxide is 6 percent.

8. The system as set forth in claim 1 wherein said bleaching gel additionally comprises a gelling agent, a thickening agent, and a neutralizing agent.

9. The system as set forth in claim 8 wherein said gelling agent is selected from the group consisting of a copolymer of acrylic acid cross-linked with polyallyl sucrose, organic polymer acid colloids selected from the group consisting of polyuronic acids, carboxypolymethylene compounds, polyester resins containing three carboxyl groups, partially hydrolyzed polyacrylates, polymethacrylates, polyoxyethylenes, polypropylene copolymers and mixtures thereof.

10. The system as set forth in claim 9 wherein said gelling agent is a copolymer of acrylic acid cross-linked with approximately 0.75 percent to 1.5 percent polyallyl sucrose.

11. The system as set forth in claim 8 wherein said neutralizing agent is selected from the group consisting of sodium hydroxide, potassium hydroxide and triethanolamine.

12. The system as set forth in claim 8 wherein said thickening agent comprises non-ionic cellulose gums selected from the group consisting of hydroxyethyl cellulose, hydroxy-propyl cellulose and carboxymethyl cellulose.

13. The system as set forth in claim 1 wherein said abrasive substance is alumina silicate particles.

14. The system as set forth in claim 13 wherein said alumina silicate has a particle size between 5 and 15 microns.

15. The system as set forth in claim 1 wherein said pigmenting agent is titanium dioxide particles.

16. The system as set forth in claim 15 wherein said titanium dioxide has a particle size of approximately 0.1 to 0.2 microns.

17. The system as set forth in claim 1 wherein said viscous polishing composition additionally comprises substances selected from the group consisting of carriers, thickening agents, surfactants, preservatives, flavor enhancers and mixtures thereof.

18. The system as set forth in claim 17 wherein said carriers comprise glycerin and water, said thickening agents comprise non-ionic cellulose gums selected from the group consisting of hydroxyethyl cellulose, hydroxypropyl cellulose and carboxymethyl cellulose, said surfactants are selected from the group consisting of polyoxyethylene (20) sorbitan monolaurate, sodium dodecyl sulfate, sodium lauryl sulfate and mixtures thereof, said preservatives selected from the group consisting of sodium benzoate, and said flavor enhancers are selected from the group consisting of sweeteners and flavoring chemicals, said sweeteners are selected from the group consisting of saccharin, sodium saccharin, methyl salicylate, sorbitol and aspartame, and said flavoring chemicals are selected from the group consisting of chemicals imparting the flavor of menthol, spearmint, wintergreen and cinnamon.

* * * * *